(12) United States Patent
Williams et al.

(10) Patent No.: US 9,115,947 B2
(45) Date of Patent: *Aug. 25, 2015

(54) APPARATUS AND METHOD FOR CLEANING THE BARREL OF A FIREARM

(71) Applicant: Otis Products, Inc., Lyons Falls, NY (US)

(72) Inventors: Nicholas Williams, Naples, FL (US); James R. Brooker, Constantia, NY (US)

(73) Assignee: Otis Products, Inc., Lyons Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,713

(22) Filed: Nov. 11, 2013

(65) Prior Publication Data

US 2014/0123530 A1    May 8, 2014

Related U.S. Application Data

(62) Division of application No. 13/785,966, filed on Mar. 5, 2013.

(60) Provisional application No. 61/724,012, filed on Nov. 8, 2012.

(51) Int. Cl.
*F41A 29/00* (2006.01)
*F41A 29/02* (2006.01)

(52) U.S. Cl.
CPC ..................................... *F41A 29/02* (2013.01)

(58) Field of Classification Search
CPC ................................ F41A 29/00; F41A 29/02
USPC .......... 42/95, 96; 15/104.05, 104.16, 104.165, 15/104.17, 104.18, 104.19
See application file for complete search history.

(56) References Cited

U.S. PATENT DOCUMENTS

| 728,302 | A | * | 5/1903 | Robbins | 89/31 |
| 739,653 | A | * | 9/1903 | Dalrymple | 401/9 |
| 1,164,665 | A | * | 12/1915 | Reeves | 15/104.16 |
| 1,172,746 | A | * | 2/1916 | Silverstein | 15/104.16 |
| 2,559,376 | A | * | 7/1951 | Schnitger | 15/104.05 |
| 3,064,294 | A | | 11/1962 | Stocking | |
| 3,100,904 | A | | 8/1963 | Stocking | |
| 3,441,419 | A | * | 4/1969 | Atterby | 106/14.13 |
| 3,682,556 | A | * | 8/1972 | Hanson | 401/132 |

(Continued)

OTHER PUBLICATIONS

Danish Patent and Trademark Office Search Report for Corresponding Turkish Application No. 2013/12857 dated May 15, 2015 (7 pgs).

*Primary Examiner* — Gabriel Klein

(74) *Attorney, Agent, or Firm* — Harris Beach PLLC

(57) ABSTRACT

A cleaning device for preserving a barrel of a firearm includes a central member defining a core and having a longitudinal length, a leading end and a trailing end. A tubular woven sheath surrounding the central member and has a lead end and a trailing end. A radial protrusion formed of a polymer is disposed about the central member between the central member and the sheath. A volatile corrosion inhibiter (VCI) is disposed on or in the cleaning device and configured to off-gas to cause a substantial part of an interior of the barrel to become lined with a protective coating to resist corrosion. The cleaning device is configured to be stored within the barrel of the firearm. A method for storing a cleaning device within a barrel of a firearm for preserving a barrel of a firearm is also described.

10 Claims, 8 Drawing Sheets

(56) References Cited

U.S. PATENT DOCUMENTS

| | | | |
|---|---|---|---|
| 3,708,820 A | 1/1973 | Schultea | |
| 3,765,045 A | 10/1973 | Schneider et al. | |
| 4,010,565 A | 3/1977 | DiProspero | |
| 4,222,142 A | 9/1980 | DiProspero | |
| 4,344,278 A | 8/1982 | Jamison et al. | |
| 4,509,223 A | 4/1985 | Sipple et al. | |
| 4,606,183 A | 8/1986 | Riggs | |
| 4,716,673 A | 1/1988 | Williams et al. | |
| 4,962,607 A * | 10/1990 | Baldwin | 42/95 |
| 5,171,925 A | 12/1992 | Mekler | |
| 5,357,705 A | 10/1994 | Stengel | |
| 5,588,242 A | 12/1996 | Hughes | |
| 5,871,589 A | 2/1999 | Hedge | |
| 5,934,000 A | 8/1999 | Hayes, Sr. | |
| 5,972,125 A | 10/1999 | Hedge | |
| 6,389,978 B1 * | 5/2002 | Hooper et al. | 102/442 |
| 6,630,034 B1 | 10/2003 | Schnell | |
| 6,640,480 B2 | 11/2003 | Williams et al. | |
| 7,356,961 B2 | 4/2008 | Williams | |
| 8,186,092 B2 | 5/2012 | Williams | |
| 8,250,800 B1 | 8/2012 | Johnson | |
| 8,371,441 B2 | 2/2013 | Williams | |
| 8,448,370 B2 | 5/2013 | Williams | |
| 2005/0118375 A1 * | 6/2005 | Damiano | 428/36.1 |
| 2006/0162223 A1 * | 7/2006 | Whipple | 42/95 |
| 2006/0288625 A1 | 12/2006 | Williams | |
| 2011/0099880 A1 * | 5/2011 | Stephens et al. | 42/95 |
| 2012/0198747 A1 | 8/2012 | Niebling | |

* cited by examiner

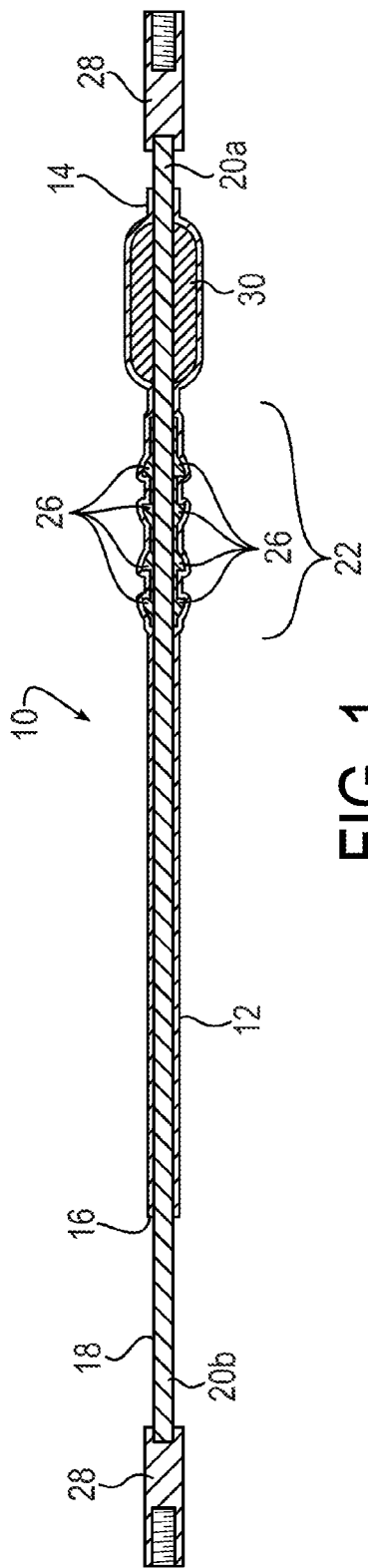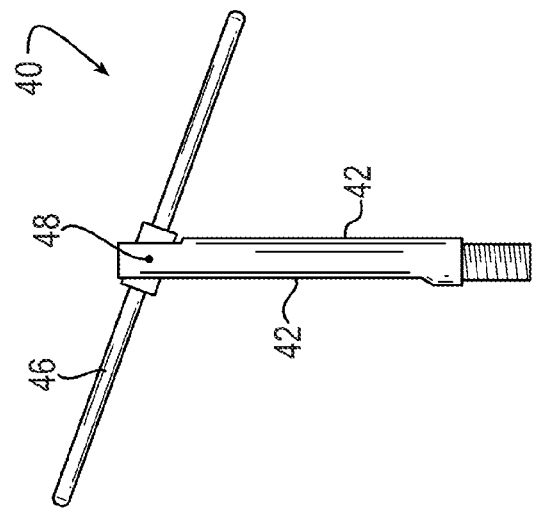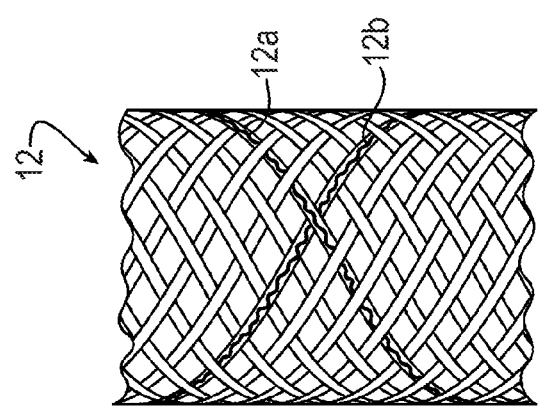

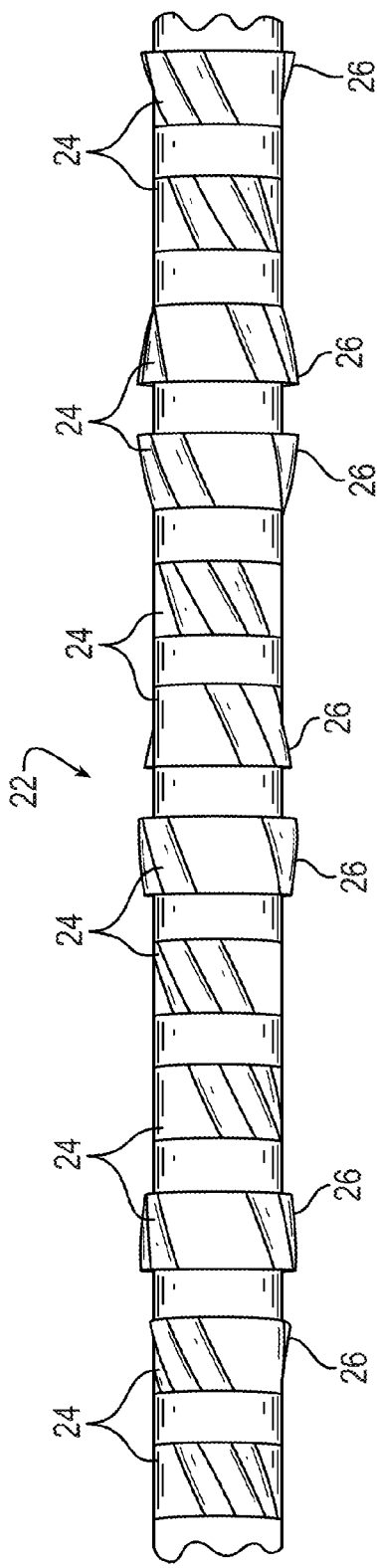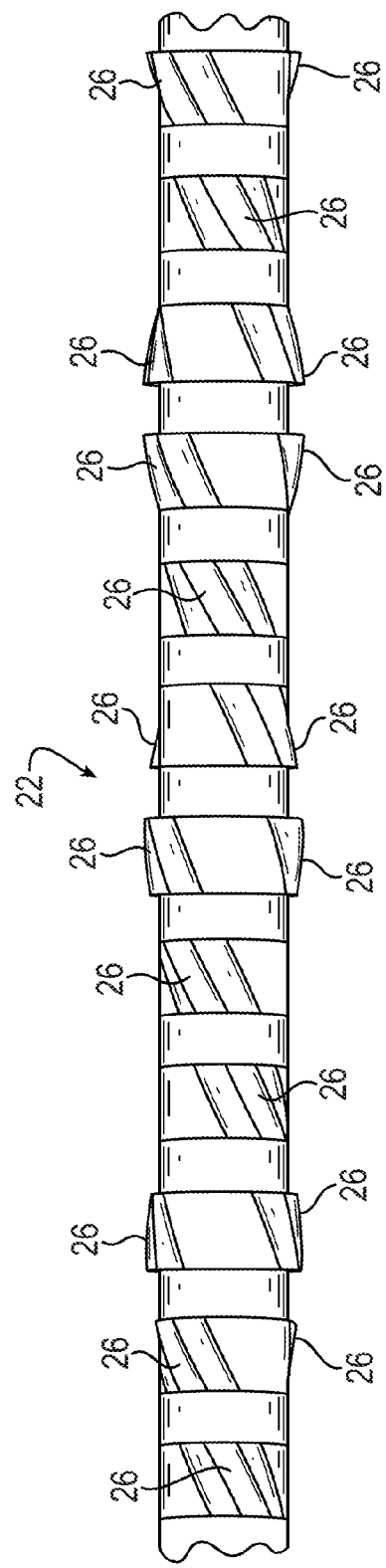

APPARATUS AND METHOD FOR CLEANING THE BARREL OF A FIREARM

This application claims priority to and the benefit of co-pending U.S. patent application Ser. No. 13/785,966, APPARATUS AND METHOD FOR CLEANING THE BARREL OF A FIREARM, filed on Mar. 5, 2013 which claims priority to and the benefit of U.S. provisional patent application Ser. No. 61/724,012, APPARATUS AND METHOD FOR CLEANING THE BARREL OF A FIREARM, filed on Nov. 8, 2012, which applications are incorporated herein by reference in their entirety.

FIELD OF THE INVENTION

The invention relates to a cleaning tool and particularly to a cleaning tool which is stored in the barrel of a firearm.

BACKGROUND OF THE INVENTION

Barrels of firearms are difficult to clean. Carbon and other residue from gunpowder and from firearm discharge reactions accumulate in firearm barrels, with deleterious effects on cleanliness, performance, and longevity of the firearm. Such residues require partial disassembly of a weapon to access and clean the barrel and associated firing chamber. A number of specialized swabbing, brushing and scraping tools have been introduced to clean firearm components, but have had substantial shortcomings.

SUMMARY OF THE INVENTION

According to one aspect, a cleaning device for preserving a barrel of a firearm includes a central member defining a core and having a longitudinal length, a leading end and a trailing end. A tubular woven sheath surrounding the central member and has a lead end and a trailing end. A radial protrusion formed of a polymer is disposed about the central member between the central member and the sheath. A volatile corrosion inhibitor (VCI) is disposed on or in the cleaning device and configured to off-gas to cause a substantial part of an interior of the barrel to become lined with a protective coating to resist corrosion. The cleaning device is configured to be stored within the barrel of the firearm. When stored in the barrel to inhibit corrosion, the cleaning device further acts as a safety flag or marker to indicate that there is or could be no round of ammunition in the chamber of the weapon.

In one embodiment, the VCI is molded or extruded within at least a portion of the sheath.

In another embodiment, the VCI is molded or extruded within at least a portion of one or more fibers of the sheath.

In yet another embodiment, the VCI is molded or extruded within at least a portion of a plastic protective coating of the central member.

In yet another embodiment, the device further includes an overmolded thermoplastic elastomer wherein the VCI is molded or extruded within at least a portion of the overmolded thermoplastic elastomer.

In yet another embodiment, the device includes two overmolded thermoplastic elastomer areas configured to fit substantially tightly within the barrel to protect the barrel from corrosion during extended periods of storage.

In yet another embodiment, the device includes an absorbent area wherein the VCI is molded or extruded within at least a portion of the absorbent area.

In yet another embodiment, the device includes two absorbent areas configured to fit substantially tightly within the barrel to protect the barrel from corrosion during extended periods of storage.

In yet another embodiment, the sheath includes an abrasive selected from the group consisting of nylon, polystyrene, acetals, acrylics, and brass.

In yet another embodiment, the sheath includes heat resistant materials selected from the group consisting of meta-aramids, NOMEX, para-aramids, KEVLAR, fiberglass, and K-fiber.

In yet another embodiment, the sheath includes a fiber selected from the group consisting of fiber-optic, luminescent and phosphorescent configured to provide for auxiliary lighting for visual inspection of the barrel.

According to another aspect, a method for preserving a barrel of a firearm includes the steps of: providing a cleaning device having a volatile corrosion inhibiter (VCI) disposed on or in the cleaning device, the cleaning device including a central member, a tubular woven sheath, and a radial protrusion; storing the cleaning device in the firearm; and off-gassing to cause a substantial part of an interior of the barrel to become lined with a protective coating to resist corrosion.

BRIEF DESCRIPTION OF THE DRAWINGS

The features described herein can be better understood with reference to the drawings described below. The drawings are not necessarily to scale, emphasis instead generally being placed upon illustrating the principles of the invention. While the particular embodiments are described in relation to cleaning the interior of a gun barrel, individuals skilled in the art will recognize and understand that the disclosure and embodiments herein are equally applicable to cleaning pipes, conduits and tubing that is both straight and curved. In the drawings, like numerals are used to indicate like parts throughout the various views:

FIG. 1 is a longitudinal cross-sectional view of a gun barrel cleaning apparatus in accordance with the present invention;

FIG. 2 is an elevational view of a portion of a tubular woven sheath in accordance with the present invention;

FIG. 3 is an elevational view of a foldable T-handle, also referred to interchangeably herein as a "pull-through handle tool", formed for passage in folded configuration through the barrel of a weapon;

FIG. 4A is an elevational view of a portion of the apparatus shown in FIG. 1 showing a central core having a feature comprising a plurality of radial protrusions;

FIG. 5 is a photographic depiction of the central core and feature shown in FIG. 4A;

DETAILED DESCRIPTION OF THE INVENTION

Figure 4B:
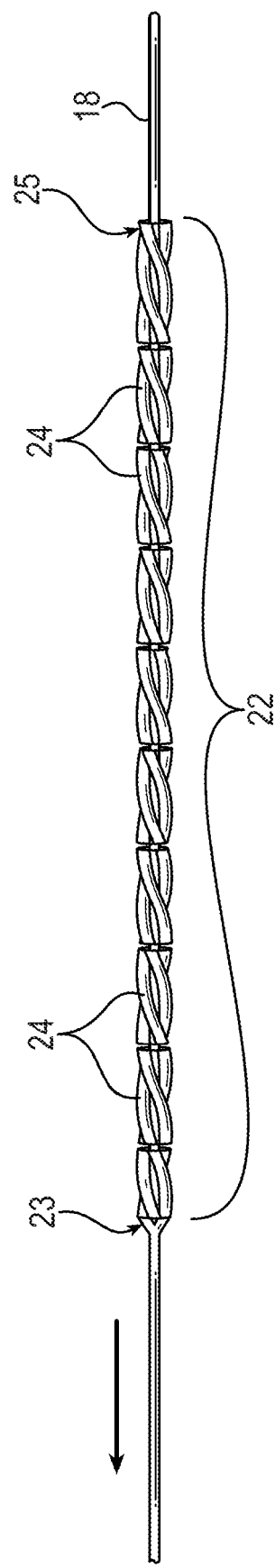
FIG. 4B is an elevational view of another embodiment of the portion of the apparatus shown in FIG. 4A comprising a central core having an overmolded plurality of helical radial protrusions.

A system and tool for cleaning the interior of tubular members is described hereinbelow. In one embodiment, a cleaning device includes a central core supporting a region of overmolded elastomer around the cable core. The system may also include a tubular woven sheath surrounding at least a portion of the overmolded elastomer. The central core may include a fitting at one end and preferably at both ends for attachment to any of various auxiliary tools such as swabs, brushes, scrapers, handles, adapters and the like. The system and tools described herein are suitable for the cleaning of the barrels of firearms, such as the barrels of rifles, carbines, pistols.

Referring to FIGS. 1 and 2, an apparatus 10 (also referred to herein as a "tool" or "gun barrel cleaner") for cleaning the barrel of a weapon or other tubular member comprises a tubular woven sheath 12 having a lead end 14 and a trailing end 16 as defined by passage of the apparatus through the barrel. Tool 10 may be passed through a barrel in either direction although it is preferable to pass the tool from the firing chamber toward the muzzle of the barrel to reduce the accumulation of dislodged residue in the firing and loading mechanisms within the chamber and receiver of the firearm and reduce the incidence of failure of such mechanisms. An elongate central member 18 defines a core disposed within tubular woven sheath 12 and generally extending the length of sheath 12 and, in one embodiment, some length 20a, 20b beyond one or both ends of sheath 12.

With reference to FIGS. 4A and 4B, a region 22 of central member 18 is provided with one or more attached feature 24 (or plurality of features 24) formed of a polymer. The leading end of the region 23 of the overmolded material may have a tapered form to reduce the likelihood of the leading end catching on debris, accumulated deposits, rifling within a barrel or a joint between adjoining sections of pipe or other tubular members, and the tool 10 is threaded or pulled through the tubular member in the direction of the arrow in FIG. 4B. Feature 24 is preferably formed of a thermosetting rubber polymer by injection overmolding onto the central member 18 having a longitudinal length. A wide variety of thermoplastic elastomers may be used. In one preferred embodiment the thermoplastic elastomer has a Shore A durometer hardness of approximately 60. Each feature 24 extends at least partially, and preferably fully, around central member 18 and radially distends the overlying region of sheath 12 to approximately the diameter of any specific caliber gun barrel, or range of gun barrel calibers, that tool 10 is intended to clean. Depending on the presence and/or thickness of the sheath and the elasticity of the polymer, the outer diameter of the protrusions may be slightly less than or slightly greater than the diameter of the barrel or other tubular member intended to be cleaned by the tool. Successive features 24 are preferably disposed in progressive angular rotation about central member 18. Each feature 24 is provided with at least one, and preferably two, radial protrusions 26. Preferably, feature 24 is provided as a plurality of substantially similar sub-features 24 helically oriented around central member 18 such that successive protrusions 26 urge the overlying fibers of sheath 12 to engage and follow the rifling lands in the barrel inner surface. The resulting twisting action imparted to sheath 12 provides superior cleaning of both the leading and trailing sides of each rifling land. The orientation of helical protrusions may be in either the same direction as or counter to the rifling of the gun barrel. The preferred helical orientation of the protrusions reduces the incidence of excess accumulations of dislodged residue forming along an annular protrusion that might otherwise result in jamming of the tool within a barrel or other tubular member. The region of the central member provided with protrusions may be adjacent the leading edge, the trailing edge or the middle portion of the tool. In another aspect of the invention, the tool may include more than a single portion provided with protrusions.

Central member 18 may comprise any material or elongate form, e.g., fiber rope or cord, rod, wire, or twisted or braided cable and may be rigid, semi-rigid or semi-flexible. The rigid or semi-rigid structure of tool 10 makes it an excellent gun barrel obstruction remover. It is preferable for the central member to have sufficient rigidity to be easily threaded or passed through the tubular member. A currently preferred material and form are a cable formed of a metal such as galvanized steel, preferably formed to have a natural curl for ease of laterally coiling in storage and preferably having a protective plastic coating. The protective plastic coating reduces the risk of scratching gun components and the potential for fraying of the cable. With respect to the cleaning of tubular members other than gun barrels, a semi-rigid structure of the core may accommodate some slight or eventual curves in the interior of a pipe, conduit or tube. However, a semi-flexible core member is preferable for cleaning sections of pipe, conduit or tubes having substantially curved shapes and turns between straight segments of tubular members.

Figure 6:
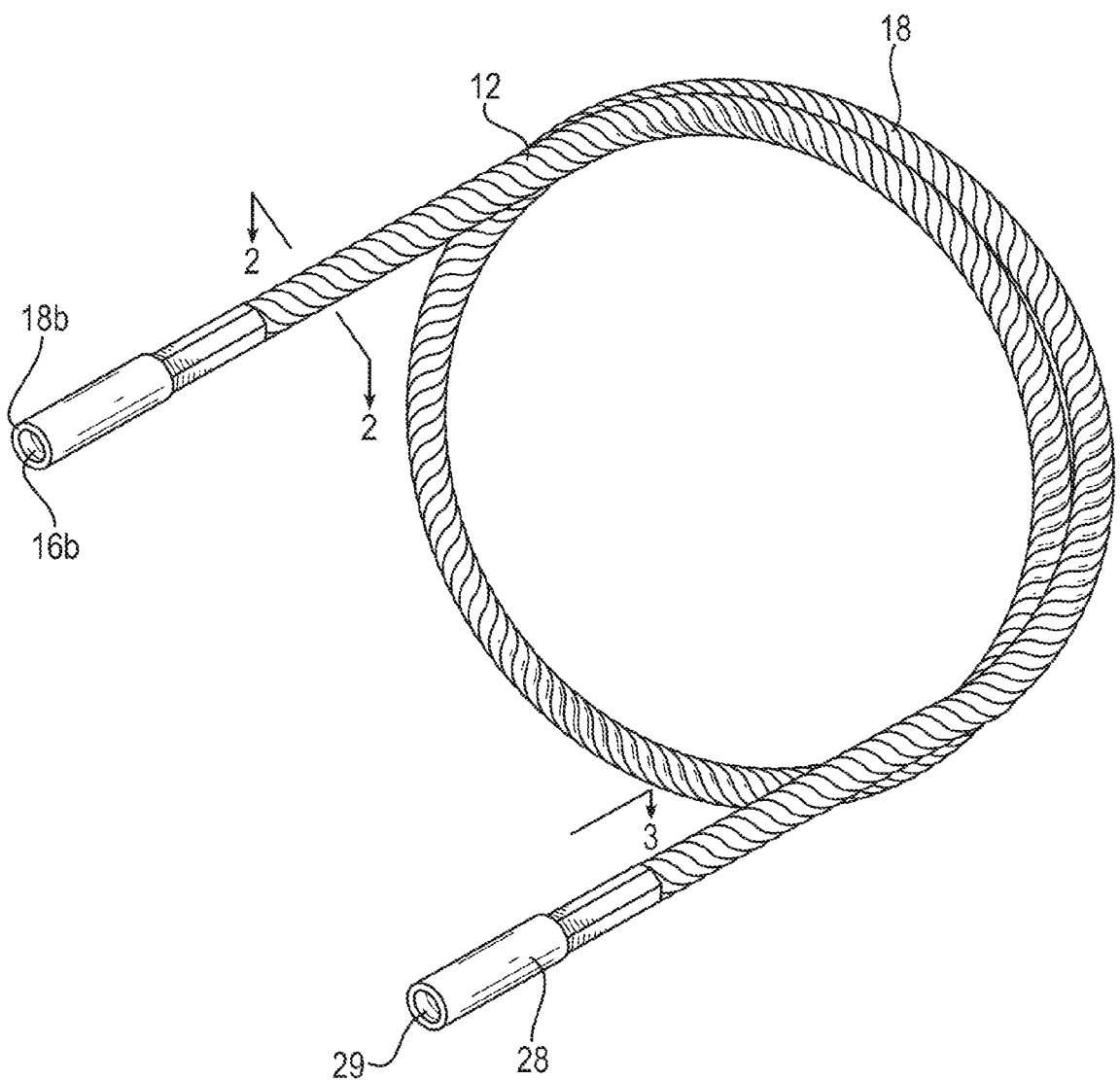
FIG. 6 depicts an embodiment of a central member having fittings on the leading and trailing ends thereof in a coiled position.

FIG. 5 shows an illustration of the central core and feature shown in FIG. 4A. FIG. 6 shows an embodiment of a central member having fittings on the leading and trailing ends thereof in a coiled position.

Figure 7:
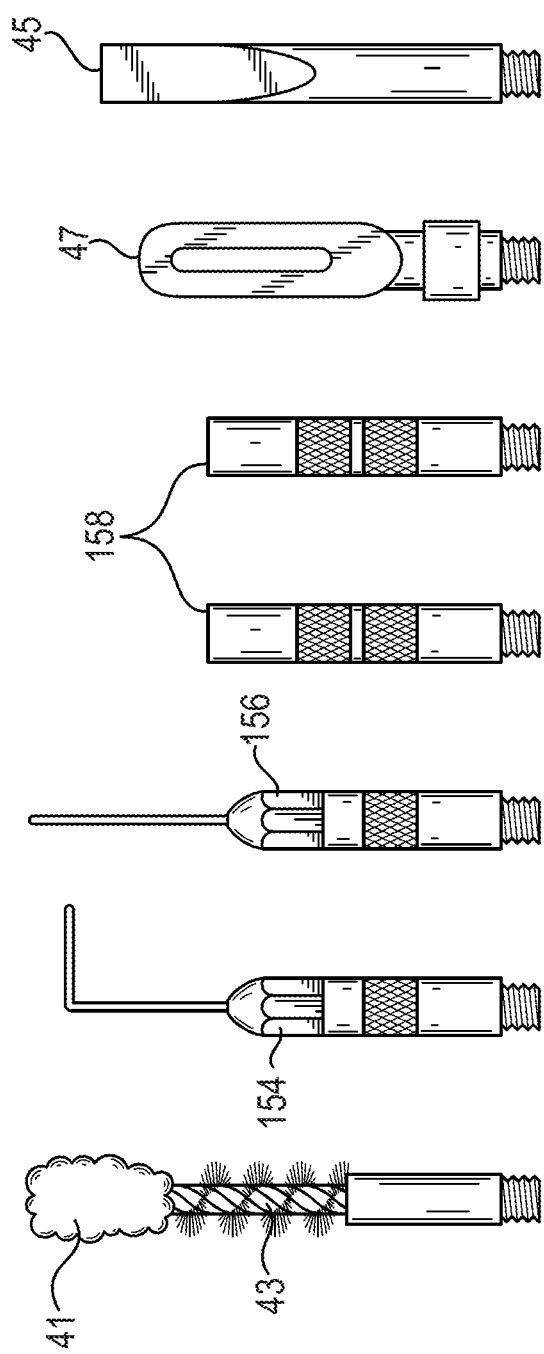
FIG. 7 depicts an assortment of typical auxiliary tools adapted to attach to the fittings at the end of the central member.
Figure 9A:
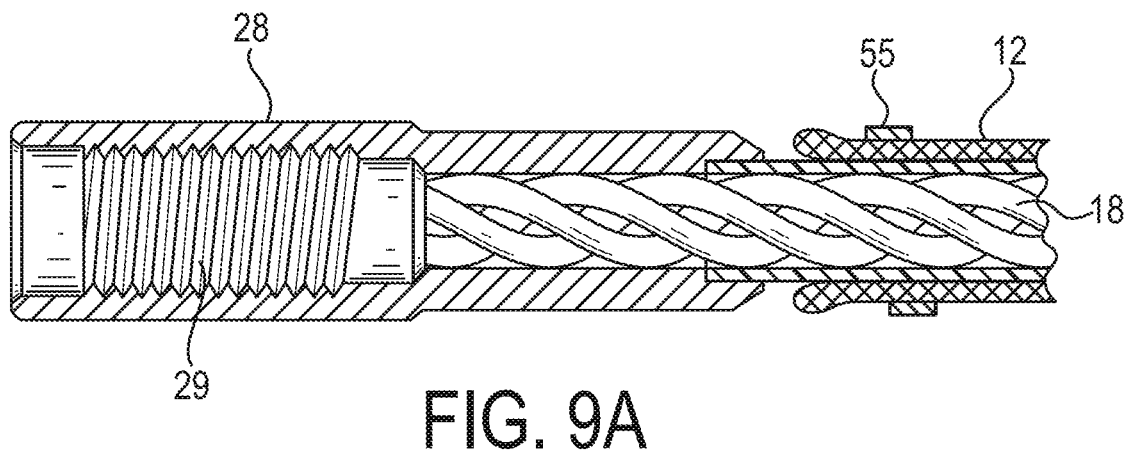
FIG. 9A depicts a crimping ring retaining the tubular woven sheath on the central member.
Figure 9B:
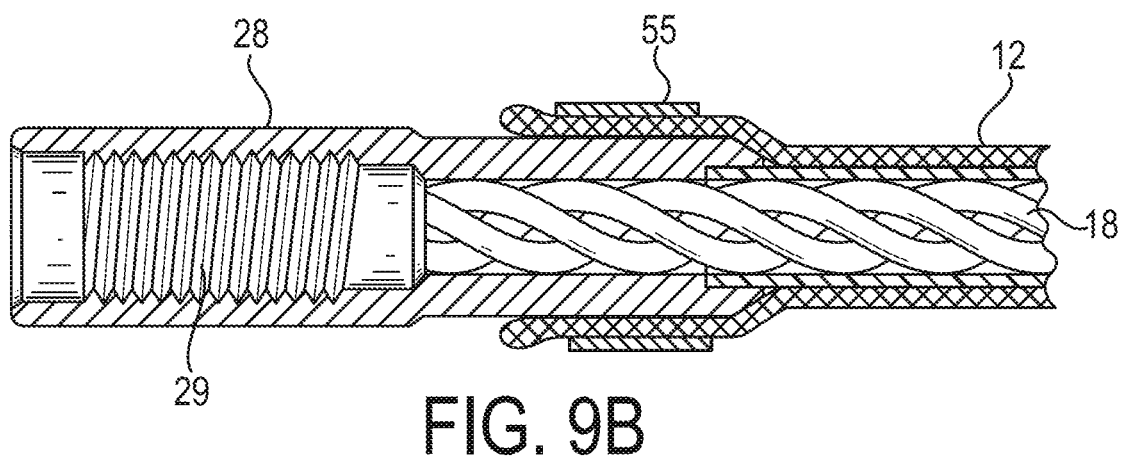
FIG. 9B depicts another embodiment wherein the crimping ring retains the sheath against a fitting at the end of the central member.

With reference to FIGS. 7, 9a and 9b, central member 18 preferably includes a fitting 28 at one end, and preferably at both ends, for attachment to any of various auxiliary tools such as swabs 41, brushes 43, scrapers 45, tips 47, a T-handle 51, and the like, as well as a cable extender and/or serially connection additional gun barrel cleaning tools 10. The fittings may be crimped, bonded or cold welded to the end of the central member. The fittings 28 may have internal or external threads 29 or other quick connect mechanisms to couple with the fittings of the auxiliary tools as depicted in FIG. 7.

In one embodiment, the fittings 28 may also be sized and configured to attach one or both of the leading or trailing end of the sheath to the central member. Alternatively, as depicted in FIGS. 9a and 9b, a separate crimping ring 55 or other suitable connector may be utilized over the sheath 12 and the central member 18 or the fitting 28 to retain the edge of the sheath in place over the central core 18, overmolded protrusions 26 and absorbent material 53.

In another aspect of the invention, the sheath 12 is not connected to the fittings or central member 18, but held in place by the tight fit of the woven sheath 12 over the protrusions 26. In another aspect, the sheath may be removable from the tool for cleaning to remove build-up of removed residue. The sheath 12 may include elasticized threads to assist in the removal, cleaning and/or replacement of the sheath. Alternatively, cleaning may be accomplished by soaking the coiled tool in a suitable detergent solution and rinsed to remove the accumulated build-up of dislodged residue.

Preferably, sheath 12 is woven of primarily a natural fiber such as cotton, although synthetic fiber may be included; and 100% synthetic fiber is fully comprehended by the invention. Many natural fibers are sufficiently absorbent to retain adequate amounts of cleaning solvent without the need for sections of additional absorbent sponges between the sheath and the core. Additional special-purpose threads, such as fiber-optic 12a, phosphorescent or luminescent threads 12b, may also be woven into the sheath to provide, for example, auxiliary lighting for visual inspection of a gun barrel for cleanliness as tool 10 is withdrawn. In another aspect of the invention, the woven sheath may comprise fibers of heat resistant materials, such as meta-aramids, NOMEX, para-aramids, KEVLAR, fiberglass, K-fiber, or the like. In another aspect of the invention, synthetic fibers, such as nylon, polystyrene, acetals, acrylics or the like, or metallic thread, such as brass or the like, may be incorporated into the sheath to increase the abrasive characteristic of the sheath to assist in removal stubborn residue from the barrel. Sheath 12 may be woven, for example, on a tubular commercially available braiding machine In another aspect of the invention, where the sheath is comprised of heat resistant fibers or materials, cleaning of the sheath could be performed by the application of sufficient heat to burn off the accumulated reside. For example, the tool 10 or the sheath 12 could be placed in an oven at a temperature below the melting or deformation temperature of the fibers such that any dirt or carbon residue detaches from the fibers of the sheath.

Figure 8:
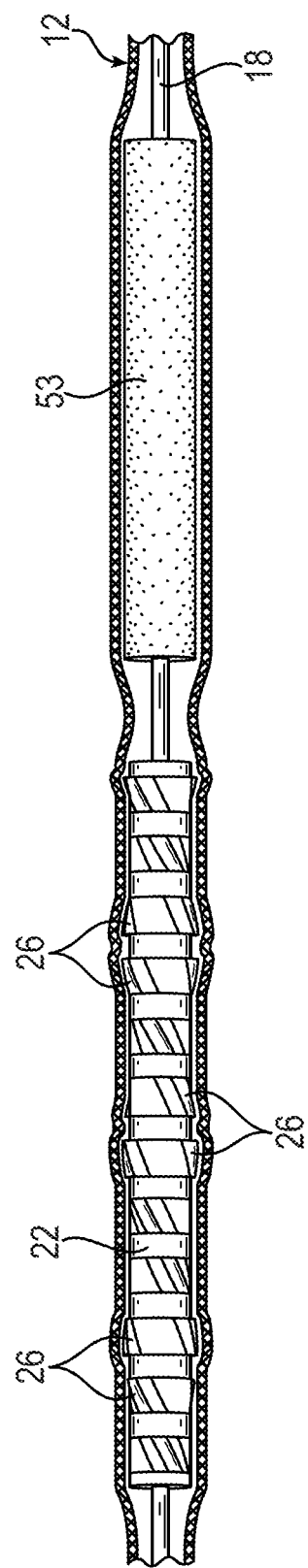
FIG. 8 depicts a cylindrical section of sponge or other absorbent material.

FIG. 8 shows a cylindrical section of sponge or other absorbent material. Preferably, additional absorbent material, such as a thin cylindrical sponge 53 may disposed about the central member and may be placed between the central member and the sheath. In one embodiment, at least one section of absorbent material is disposed about the central member at the lead end thereof, ahead of overmolded thermoplastic region 22 to assist in the application of cleaning solvent to the accumulated deposits or residue within a gun barrel. In another aspect of the invention, a second area of sponge material is disposed within the sheath adjacent to trailing end thereof to apply an even coating of lubricant or other corrosion resistant fluid. The absorbent material may hold additional solvent or lubricant that is applied as the gun barrel cleaner is pulled through the barrel. In another embodiment, the natural fibers of the sheath or woven sheath are sufficiently absorbent to apply sufficient amounts of solvents and/or lubricants during the passing of the cleaner through the gun barrel in a single pass or multiple passes.

In another embodiment, the gun barrel cleaner 10 may include successive or alternating areas of overmolded protrusions 26 and/or absorbent materials 53 to perform multiple cleaning operations in a single pass of the cleaner. For example, a first area of absorbent material is disposed closer to the leading end of the cleaner to apply a cleaning solvent. A second area of absorbent material is disposed adjacent to the trailing end of the gun barrel cleaner to apply a layer of protective lubricant. In between the areas of absorbent material, at least one area of overmolded protrusions is disposed to clean or abrasively scrub the interior of the gun barrel.

In another aspect of the invention, two sections of the gun barrel cleaner may be connected through a complementary fitting and/or adapter to clean longer gun barrels. In another aspect of the invention, two sections may be connected to complementary fittings at each end of an appropriately sized bore brush where additional abrasive force may need to be supplied.

Figure 10A:
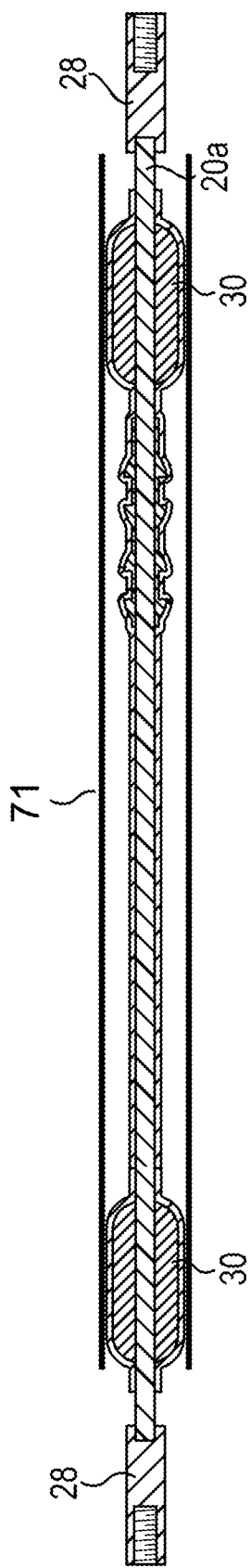
FIG. 10A depicts an embodiment where the gun cleaning tool including at least two areas of overmolded thermoplastic elastomer preserves the gun during storage.
Figure 10B:
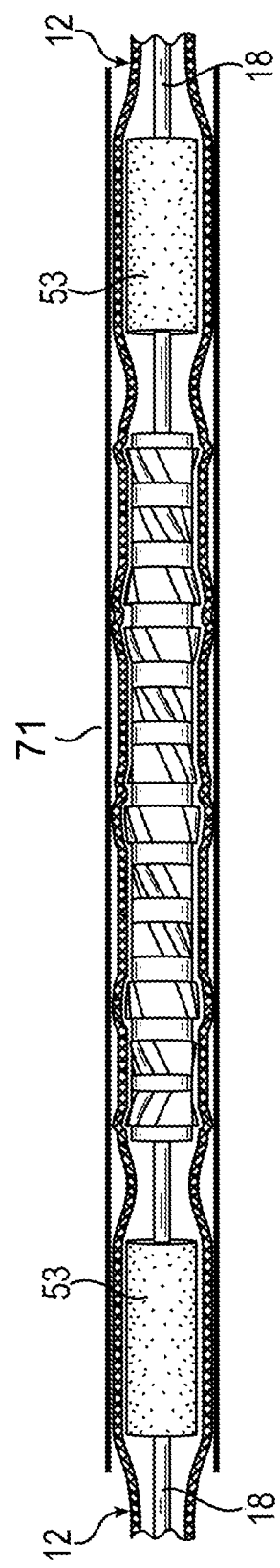
FIG. 10B depicts an embodiment where the gun cleaning tool including at least two absorbent areas preserves the gun during storage.

As shown in FIG. 10A and FIG. 10B, in another aspect of the invention, the gun cleaning tool may be used to preserve the gun during storage. Preferably, when used for such purposes, the tool will include at least two areas of either overmolded thermoplastic elastomer (e.g. two overmolded thermoplastic elastomer areas 30, FIG. 10A) or absorbent materials (e.g. two absorbent areas 53, FIG. 10B) at intervals that approximate the overall length of the gun barrel 71. At least a portion of the sheath between two areas is treated with a volatile corrosion inhibitor (VCI). Alternatively, the volatile corrosion inhibiter could be molded or extruded within the plastic protective coating of the central member or the fibers of the sheath. When the tool is stored within the barrel for extended periods of time (e.g. extended periods of storage), the volatile corrosion inhibitor will off-gas to line a substantial part of the interior of the gun barrel with a protective coating to resist corrosion. The two overmolded or absorbent areas will fit relatively tightly within the barrel to retain the off-gassed corrosion inhibitor within the barrel to protect the barrel from corrosion. When stored in the barrel to inhibit corrosion, the portion of the device beyond the two areas of either overmolded thermoplastic elastomer or absorbent materials that approximate the overall length of the gun barrel will typically protrude into the firming chamber and out of the muzzle at either end of the barrel. Therefore, when the cleaning device is used in this configuration, the device further acts as a safety flag or marker to those handling the firearm that there is or could be no round of ammunition in the chamber of the weapon, and thus is not at risk for inadvertent discharge of a round.

Referring now to FIG. 3, an exemplary foldable T-handle 40, comprising a threaded shaft 42 having a longitudinal well 44 and a pivotable handle 46 attached to shaft 42 by pin 48 formed for passage in folded configuration through the bore of a weapon, is attachable to either of fittings 28, either before or after passage through a gun barrel of a leading end of apparatus 10, to assist a user in pulling apparatus 10 through a gun barrel. Where embodiments of the invention are used to clean the interior of tubular members having curved shapes, the T-handle is preferably attached to the fitting at the leading end of the central member after it is threaded through the tubular member. Where the interior of the tubular member is straight, a slim profile T-handle may be attached to the fitting at the leading end of the central member, or may be integrated with the fitting at the leading end of the central member. An exemplary slim profile T-handle is disclosed in U.S. patent application Ser. No. 13/448,973 entitled "Firearm Pull-Through Cleaning Tool with Integrated Foldable Handle," filed on Apr. 17, 2012 assigned to the common assignee of this application, which is hereby incorporated by reference in its entirety.

The respective thicknesses of the central core, protective layer, overmolded protrusions, absorbent materials and the woven sheath may be varied to change the radial width of the tool to fit the gun barrels of differing calibers. Alternatively, the compressibility of the overmolded protrusions, absorbent material and/or the woven sheath may also be increased so that a single tool may appropriately clean a range of calibers of gun barrels.

In another aspect of the invention, the natural fibers of the sheath and any absorbent material disposed beneath the sheath or at the trailing end of the central member may be used to absorb and remove spent cleaning fluids containing dislodged residue. However, the overmolded thermoplastic region has been successfully deployed to clean a variety of relatively narrow tubular members without a sheath. The plurality of protrusions, including particularly, a pair of the helical protrusions, formed around the overmolded thermoplastic region is effective at removing liquids and semi-solids such as grease and congealed oils, from narrow drains. The plurality of protrusions wipe excess accumulations of liquids and semi-solids in the manner of a squeegee from the interior of a pipe or drain. Even where a pipe or drain includes a catch or other curved portion, embodiments of the invention utilizing a semi-flexible central member were threaded through the drain and pulled through the tubular member. This embodiment removed excess accumulations of grease and spent oils in a small fraction of the time of other common methods.

While the present invention has been described with reference to a number of specific aspects or embodiments, it will be understood that the true spirit and scope of the invention should be determined only with respect to claims that can be supported by the present specification. While the particular embodiments may have been described in relation to cleaning the interior of a gun barrel, individuals skilled in the art will recognize and understand that the disclosure and embodiments herein are equally applicable to cleaning pipes, drains, conduits and tubing that is both straight and curved. Further, while in numerous cases herein wherein systems and apparatuses and methods are described as having a certain number of elements it will be understood that such systems, apparatuses and methods can be practiced with fewer than the mentioned certain number of elements. Also, while a number of particular embodiments have been described, it will be understood that features and aspects that have been described with reference to each particular embodiment can be used with each remaining particularly described embodiment.

What is claimed:

1. A cleaning device for preserving a barrel of a firearm having rifling lands comprising:
    a central member defining a core and having a longitudinal length, a leading end and a trailing end;
    a tubular woven sheath surrounding said central member and having a lead end and a trailing end;
    at least five annular thermoplastic elastomer features disposed around said central member and spaced apart along the longitudinal length of the central member such that each feature is adjacent to another of said features, each of said features comprising at least one radial protrusion helically oriented around said central member, all of said radial protrusions having a same helical direction and substantially a same helix angle, and the radial protrusions of adjacent features being disposed in a progressive angular rotation relative to the central member such that said radial protrusions collectively form at least one discontinuous helix having discontinuities defined by a longitudinal space between each pair of adjacent features, wherein the radial protrusions of successive features urge a plurality of overlying fibers of said tubular woven sheath to engage and follow the rifling lands of an inner surface of said barrel of said firearm, wherein said features are disposed separately along said central member between said central member and said tubular woven sheath, and wherein the tubular woven sheath is held in place by a tight fit of the tubular woven sheath over the radial protrusions
    a first area of thermoplastic elastomer or absorbent material disposed about said central member at about said leading end, and a second area of thermoplastic elastomer or absorbent material disposed about said central member at about said trailing end spaced apart by about the length of said barrel of a firearm, said at least five annular thermoplastic elastomer features disposed along said central member between said first area of thermoplastic elastomer or absorbent material and said second area of thermoplastic elastomer or absorbent material, said first area of thermoplastic elastomer or absorbent material and said second area of thermoplastic elastomer or absorbent material being separate structures not a part of any of said at least five annular thermoplastic elastomer features;
    a volatile corrosion inhibiter (VCI) disposed between said leading end and said trailing end and configured to off-gas to cause a substantial part of an interior of said barrel to become lined with a protective coating to resist corrosion; and
    wherein said cleaning device is configured to be stored within said barrel of said firearm and said first area of thermoplastic elastomer or absorbent material and said second area of thermoplastic elastomer or absorbent material fit tightly within said barrel of said firearm to retain said VCI within said barrel of said firearm during a storage period.

2. The device of claim 1, wherein said VCI is molded or extruded within at least a portion of said sheath.

3. The device of claim 2, wherein said VCI is molded or extruded within at least a portion of one or more fibers of said sheath.

4. The device of claim 1, wherein said VCI is molded or extruded within at least a portion of a plastic protective coating of said central member.

5. The device of claim 1, further comprising an overmolded thermoplastic elastomer area between said leading end and said trailing end, wherein said VCI is molded or extruded within at least a portion of said overmolded thermoplastic elastomer area.

6. The device of claim 1, further comprising an absorbent area between said leading end and said trailing end, wherein said VCI is molded or extruded within at least a portion of said absorbent area between said leading end and said trailing end.

7. The device of claim 1 wherein said sheath comprises an abrasive selected from the group consisting of nylon, polystyrene, acetals, acrylics, and brass.

8. The device of claim 1 wherein said sheath comprises heat resistant materials selected from the group consisting of meta-aramids, NOMEX, para-aramids, KEVLAR, fiberglass, and K-fiber.

9. The device of claim 1 wherein said sheath includes a fiber selected from the group consisting of fiber-optic, luminescent and phosphorescent configured to provide for auxiliary lighting for visual inspection of said barrel.

10. The device of claim 1, wherein said first area of elastomer or absorbent material and said second area of elastomer or absorbent material are between the central member and the sheath.

* * * * *